United States Patent
Leen et al.

(10) Patent No.: US 9,915,562 B2
(45) Date of Patent: Mar. 13, 2018

(54) METHOD OF INCREASING POWER WITHIN AN OPTICAL CAVITY WITH LONG PATH LENGTHS

(71) Applicant: ABB, Inc., Cary, NC (US)

(72) Inventors: John Brian Leen, Sunnyvale, CA (US); Nathan E. Bramall, Sunnyvale, CA (US)

(73) Assignee: ABB, INC., Cary, NC (US)

( * ) Notice: Subject to any disclaimer, the term of this patent is extended or adjusted under 35 U.S.C. 154(b) by 0 days.

(21) Appl. No.: 15/235,401

(22) Filed: Aug. 12, 2016

(65) Prior Publication Data

US 2018/0045561 A1    Feb. 15, 2018

(51) Int. Cl.
  *G01J 5/02*    (2006.01)
  *G01J 3/02*    (2006.01)
  *G01J 3/42*    (2006.01)
  *G01N 21/3504*    (2014.01)

(52) U.S. Cl.
  CPC ............... *G01J 3/021* (2013.01); *G01J 3/42* (2013.01); *G01N 21/3504* (2013.01); *G01N 2201/06113* (2013.01)

(58) Field of Classification Search
  CPC .. G01N 21/39; G01N 16/06; G01N 2021/399; G01N 2015/0693; G01N 2021/391; G01N 21/3504; G01J 3/02; G01J 3/0218; G01J 3/42
  See application file for complete search history.

(56) References Cited

U.S. PATENT DOCUMENTS

| | | | |
|---|---|---|---|
| 5,247,562 A * | 9/1993 | Steinbach | H01S 3/0903 372/22 |
| 5,538,850 A * | 7/1996 | King | G01N 21/552 356/136 |
| 5,633,724 A * | 5/1997 | King | G01N 21/552 356/136 |

(Continued)

OTHER PUBLICATIONS

Printout: J.B. McManus et al., "Astigmatic mirror multipass absorption cells for long-path-length spectroscopy", Applied Optics, vol. 34, No. 18, Jun. 20, 1995, pp. 3336-3348 & 3 drawing sheets.

(Continued)

*Primary Examiner* — Kiho Kim
(74) *Attorney, Agent, or Firm* — Thomas Schneck

(57) ABSTRACT

A cavity-enhanced absorption spectroscopy instrument has an optical cavity with two or more cavity mirrors, one mirror of which having a hole or other aperture for injecting a light beam, and the same or another mirror of which being partially transmissive to allow exit of light to a detector. A spherical-spherical configuration with at least one astigmatic mirror or a spherical-cylindrical configuration where the spherical mirror could also be astigmatic prevents a reentrant condition wherein the injected beam would prematurely exit the cavity through the aperture. This combination substantially increases the number of passes of the injected beam through a sample volume for sensitive detection of chemical species even in less than ideal conditions including low power laser or LED sources, poor mirror reflectivity or detector noise at the wavelengths of interest, or cavity alignment issues such as vibration or temperature and pressure changes.

23 Claims, 3 Drawing Sheets

(56) References Cited

U.S. PATENT DOCUMENTS

| | | | | |
|---|---|---|---|---|
| 6,064,488 | A * | 5/2000 | Brand | G01N 21/39 356/437 |
| 6,075,252 | A * | 6/2000 | Atkinson | G01N 21/39 250/339.13 |
| 6,795,190 | B1 | 9/2004 | Paul et al. | |
| 6,839,140 | B1 | 1/2005 | OKeefe et al. | |
| 7,101,340 | B1 * | 9/2006 | Braun | A61B 5/097 128/920 |
| 7,468,797 | B1 | 12/2008 | OKeefe et al. | |
| 7,800,751 | B1 | 9/2010 | Silver et al. | |
| 7,902,534 | B2 * | 3/2011 | Cole | G01J 1/44 250/573 |
| 8,299,433 | B2 * | 10/2012 | Majewski | G01N 21/031 250/336.1 |
| 2002/0185603 | A1 * | 12/2002 | Daly | G01J 5/24 250/338.1 |
| 2006/0181710 | A1 * | 8/2006 | Kachanov | G01N 21/39 356/437 |
| 2008/0030867 | A1 * | 2/2008 | Corem | G02B 3/0031 359/641 |
| 2009/0059234 | A1 * | 3/2009 | Dreyer | G01J 3/02 356/437 |
| 2010/0141951 | A1 * | 6/2010 | Ali | B01L 3/502715 356/436 |
| 2011/0297651 | A1 * | 12/2011 | Squier | B23K 26/0624 219/121.18 |
| 2012/0060510 | A1 * | 3/2012 | Badami | G01J 3/108 60/796 |
| 2014/0117238 | A1 * | 5/2014 | McCann | G01N 21/3504 250/338.4 |
| 2015/0099274 | A1 * | 4/2015 | Axelrod | C12M 41/34 435/39 |
| 2015/0131094 | A1 * | 5/2015 | Alquaity | G01J 3/42 356/326 |

OTHER PUBLICATIONS

Printout: P.K. Dasgupta et al., "Cavity-Enhanced absorption measurements across broad absorbance and reflectivity ranges", ACS Publications, 2014 American Chemical Society, Anal. Chem. 2014, 86, pp. 3727-3734.

Printout: D.R. Herriott et al., "Folded Optical Delay Lines", Applied Optics, vol. 4, No. 8, Aug. 1965, pp. 883-889.

Printout: J.A. Silver, "Simple dense-pattern optical multipass cells", Applied Optics, vol. 44, No. 31, Nov. 1, 2005, pp. 6545-6556.

* cited by examiner

METHOD OF INCREASING POWER WITHIN AN OPTICAL CAVITY WITH LONG PATH LENGTHS

STATEMENT REGARDING FEDERALLY-SPONSORED RESEARCH AND DEVELOPMENT

This invention was made with government support under SBIR contract number DE-SC0007654, awarded by the Department of Energy. The government has certain rights in the invention.

TECHNICAL FIELD

The present invention relates to cavity-enhanced absorption spectroscopy instruments, such as integrated cavity output spectroscopy systems or cavity ringdown systems, and in particular relates to optical cavity features of such devices that provide long effective path lengths.

BACKGROUND ART

Integrated cavity output spectroscopy (ICOS) is used to measure small optical absorptions for the quantification and speciation of trace constituents. ICOS uses two or more high reflectivity mirrors to trap light and increase the effective path length. In ICOS, the light passes through the front mirror to enter the cavity and through (usually) another mirror, such as the back mirror, onto the detector. This double transmission under non-resonant conditions results in a power transmission on the order of T/2, where T is the transmission fraction of the mirrors.

The low power transmission limits instrument sensitivity and requires high power lasers and/or high gain amplifier detectors—all of which increase the cost and decrease the utility of ICOS instruments. There are several optical regions where these problems are acute. Of note, lasers operating between 3 and 4 um produce limited power, making it difficult to accurately and precisely measure the many important hydrocarbon absorptions in the region. Also, high reflectivity mirrors made to operate at wavelengths longer than about 8 um require materials in the Bragg stack that have high optical losses—the many cavity reflections that are a requirement of cavity-enhanced absorption spectroscopy (CEAS) rob the system of light, resulting in very small powers incident on the detector.

The addition of an exit hole to a standard multi-pass cell is described by Herriott et al. in "Folded Optical Delay Lines", Applied Optics 4(8), 883-889 (August 1965). The addition of a hole for the introduction of light has also been previously proposed. In an article by Dasgupta et al., "Cavity-Enhanced Absorption Measurements across Broad Absorbance and Reflectivity Ranges", Analytical Chemistry 86, 3727-3734 (2014), the merits of such an injection hole are detailed. These previously proposed embodiments succeed in increasing the transmitted power, but sacrifice path length as a result, yielding mere tens of reflections instead of the thousands common to standard CEAS. This is a result of limitations on spherical-spherical and planar-planar cavities that was recognized almost immediately after the introduction of multi-pass cells. In each of these cases, the stability conditions return the injected beam to the injection hole after a few passes where the power is passed out.

As a result, complicated astigmatic cells were invented that used either nearly spherical mirrors or clocked cylindrical mirrors, as in McManus et al., "Astigmatic mirror multipass absorption cells for long-path-length spectroscopy", Applied Optics 34(18), 3336-3348 (20 Jun. 1995); Joel A. Silver, "Simple dense-pattern optical multipass cells", Applied Optics 44(31), 6545-6556 (1 Nov. 2005). These cavities are currently used by some companies (e.g., Aerodyne, Inc) for trace gas detection.

Herriott cells have the requirement that light must be passed in through the entrance hole, reflected through the cavity and then pass out of the hole without variable loss. This limits the cavity configurations to those that have a reentrant condition, i.e., passing in and out of the same hole and makes them hard to align and operate under field conditions (vibrations, changing temperature and pressure, etc.).

SUMMARY DISCLOSURE

We have invented a method of increasing the power injected into the cavity while retaining long path lengths. The method uses a hole or reduced reflectivity area of the input mirror to introduce a much higher proportion of light than is usual (as 100-1000×) for ICOS or other CEAS methods. An astigmatic cavity configuration similar to an astigmatic Herriott cell is used to prevent the beam from exiting the cavity after only a few reflections. The present invention differs from standard multipass cells in that we collect the light through the exit mirror without a hole, via transmission through the reflective coating. This approach allows the use of lower power lasers or LEDs or broadband light sources, poor mirror coatings, high noise detectors and any other situation where the system performance is limited by insufficient power on the detector. It reduces the light intensity at the detector, but significantly simplifies alignment and allows us to use a wide range of alignments and mirror configurations.

Accordingly, a cavity-enhanced absorption spectroscopy instrument in accord with the present invention comprises an optical cavity defined by at least two cavity mirrors and containing a sample volume. An optical aperture is formed in one of the cavity mirrors. The same or a different one of the cavity mirrors is partially transmissive of light, such that a detector is positioned to collect light passing through that partially transmissive cavity mirror. A tunable-wavelength light source supplies a light beam directed through the aperture in the first cavity mirror so as to be injected into the optical cavity. At least one of the cavity mirrors is also characterized as having an astigmatism selected such that the light beam in the cavity is prevented from exiting the cavity through the aperture until passing some minimum number of multiple times through the sample volume. This minimum number will be more than is possible with a spherical-spherical or planar-planar configuration as found in prior art.

In one embodiment, the optical cavity may comprise a two-mirror cavity having two substantially spherical mirrors, wherein at least one of the mirrors is characterized by a specified amount of astigmatism. In particular, the longest and shortest radii of curvature of the astigmatic spherical mirror may differ by at least 1%. In another embodiment, the first mirror may have a substantially spherical curvature (with or without some degree of astigmatism), while the second mirror has a cylindrical curvature so that the optical cavity has a two-mirror spherical-cylindrical configuration. In yet another embodiment, at least one of the mirrors might be aspheric and/or conic with a central region flattened relative to a peripheral region such that the light beam multi-path has lower mode density at the center of the cavity.

In another embodiment, at least one of the mirrors is aspheric with a peripheral region that is flattened relative to the central region to decrease the mode density on the periphery. The mirror curvatures and separation of the mirrors are preferably selected such that the optical cavity is a stable cavity; although in one possible embodiment, the cavity might be stable in one dimension but a Fabry-Perot cavity in an orthogonal dimension. With any of these configurations, the number of passes of the light beam through sample volume should be at least in excess of 30, but in some embodiments could be in excess of 300.

The number of passes may be enhanced by embodiments having the light beam directed through the aperture at a tilt angle greater than 0.5° and selected to maximize the number of passes. Likewise, in some embodiments, the aperture could be located off of a central axis of the cavity, i.e. off-axis injection of the light beam.

The first cavity mirror having the aperture may be a highly reflective dielectric-coated mirror with transmissivity of less than 10 parts per million, except of course at the aperture. The aperture can be a hole through the mirror or a transmissive or partially transmissive region of the mirror. The partially transmissive mirror of the optical cavity will still be mostly reflective to allow multiple passes of the beam through the sample volume in the cavity. For example, in one possible embodiment, the partially reflective mirror may have a reflectivity of at least 98% and a transmissivity of at most 2%. (Assuming a perfectly reflective first mirror and ignoring sample absorption, such a partial reflectivity will reduce light intensity by one-half after 35 round trips.)

The invention is preferably included in one or more trace gas analyzers for which the optical absorptions are large. The expected principal use of this application is as a modification to integrated cavity output spectroscopy (ICOS) at wavelengths with poor laser power, poor mirror coatings, high noise detectors or any combination of the three. ICOS is used for the detection of trace gas species in industrial process monitoring, medical diagnostics, environmental research, etc. For example, it may be offered in carbon isotope instruments operating near 2 and 4.3 um, or in $N_2O/CO$ concentration analyzers. The most immediate applications may include 3-4 um detection of hydrocarbons using low power, inter-band cascade lasers (ICLSs), measurement of high absorption strength $CO_2$ carbon isotope lines near 4.3 um and measurement of $NH_3$, formaldehyde and VOCs beyond 8 um where mirror coatings are strongly absorbing. Alternatively, if the light source is pulsed, the instrument could be operated in a cavity ring-down mode.

For each of FIGS. 2 through 5, for these representative embodiments, injection is in the center of the mirror, the cavity is 52 cm long, and the injection mirror is spherical with a 1 m radius of curvature, giving a stability parameter $g_1=(1-d/R)$ for the cavity's injection mirror of 0.48.

DETAILED DESCRIPTION

Figure 1:
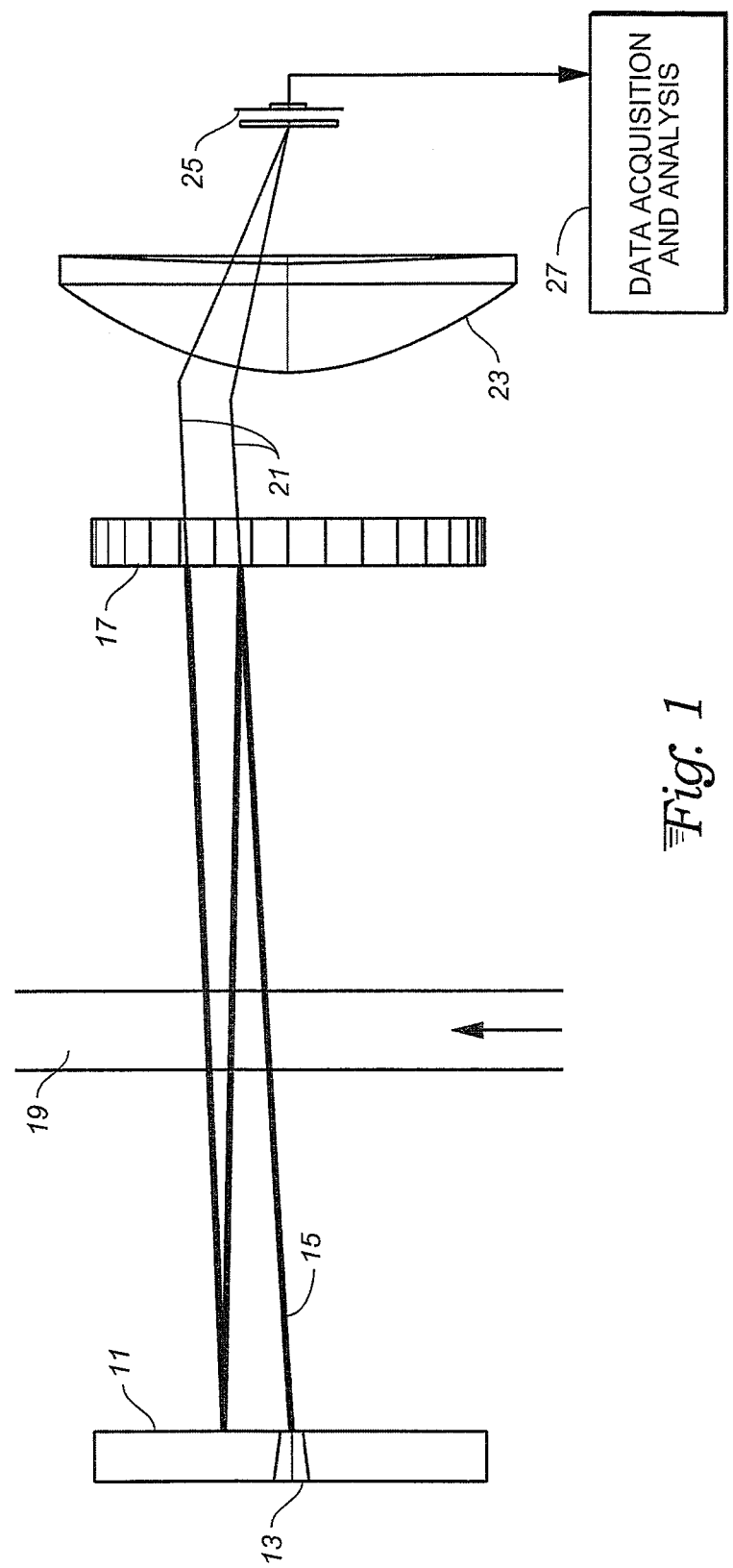
FIG. 1 is a diagram of an embodiment of the invention with two mirrors and a central injection hole. Either the exit mirror or the injection mirror must be astigmatic.

With reference to FIG. 1, our invention utilizes an astigmatic cavity configuration similar to an astigmatic Herriott cell to prevent the beam from exiting the cavity after a few reflections. A first mirror 11 has an injection hole 13 so that the mirror 11 serves as an injection mirror for the optical cavity. A light source (not shown) is located outside of the cavity and provides a light beam 15 that is directed through the injection hole 13 into the cavity. A second mirror 17 spaced apart from the injection mirror 11 is partially transmissive of the light beam 15. The light beam 15 makes multiple round trips within the cavity and passes through a sample volume 19 some minimum number of times so as to be subject to absorption by any gaseous or vapor sample within the sample volume 19. Light 21 transmitted partially through the mirror 17 is collected, for example by a lens 23, so as to impinge upon and be detected by a detector 25.

The signal output from detector 25 is coupled into a data acquisition and analysis system 27. The analysis performed by that system on the detection data determines a wavelength-dependent absorption of the sample passing through the cavity sample volume 19. Then, using the derived absorption spectrum, the analysis system can identify one or more component chemical species present in the sample and determine their respective concentration levels. The determination of wavelength-dependent absorption may be performed in an integrated cavity output spectroscopy (ICOS) mode of operation, or alternatively using a cavity ring-down spectroscopy (CRDS) technique. These are known methods of cavity-enhanced absorption spectroscopy (CEAS) measurement described in published technical literature, including but not limited to U.S. Pat. Nos. 6,795,190, 6,839,140 and 7,468,797. Any such CEAS technique may be used to obtain the sample's absorption spectrum from the detector signal. A database of known absorption spectra may be employed to identify component species in the sample. The system may also be calibrated using various reference samples, especially for any particular species of interest, in order that the correspondence between absorption level and component species concentration may be accurately ascertained.

The mirrors 11 and 13 (as well as any other cavity mirrors) together form a stable cavity configuration. This includes cases where both mirrors are substantially spherical, one mirror is substantially spherical and another is substantially cylindrical, or one or both mirrors have conic or other aspherical curvature. In the case of dual spherical mirrors, at least one of the mirrors will have a certain amount of astigmatism (e.g. 1%) to prevent a reentry condition wherein the injected light beam prematurely exits the cavity back through the hole 13. Other cavity configurations are also possible, including ring cavities with three or more mirrors, as well as having the injection mirror and partially transmissive mirror be the same mirror of the multi-mirror optical cavity.

Figure 2:
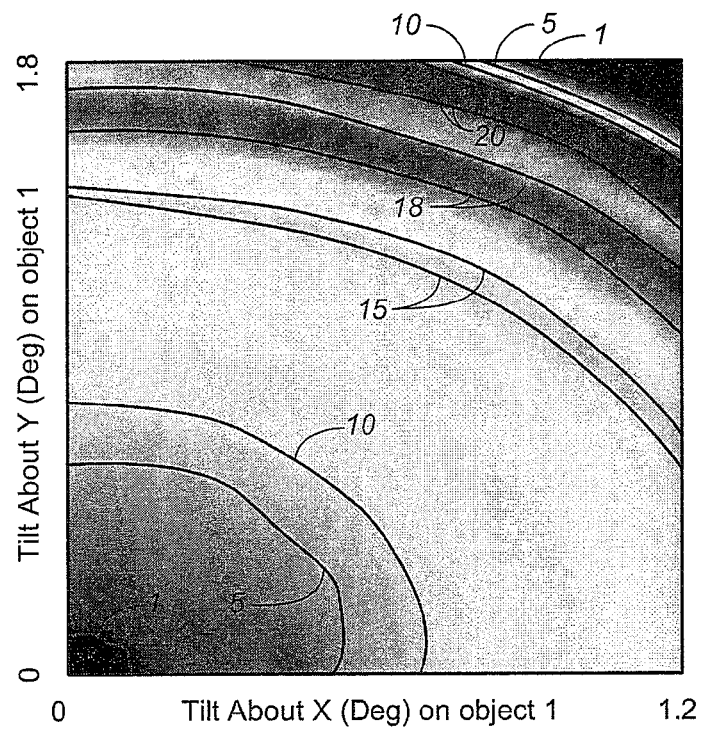
FIG. 2 is a graph showing the number of passes vs. injection angle in a cavity using our invention with a perfectly spherical exit mirror. In this example, the spherical exit mirror has a 1 m radius of curvature.

The number of passes vs. injection angle for a prior art spherical-spherical configuration (without astigmatism) is shown in FIG. 2 and reaches a maximum of about 21. One will note that the number of passes depends upon the tilt angle of the injected beam relative to a central axis passing through the centers of both mirrors. Tilt angles close to one percent tend the most number of passes, while near axial injection tends to leave the cavity fairly rapidly after 10 or fewer passes.

Figure 3:
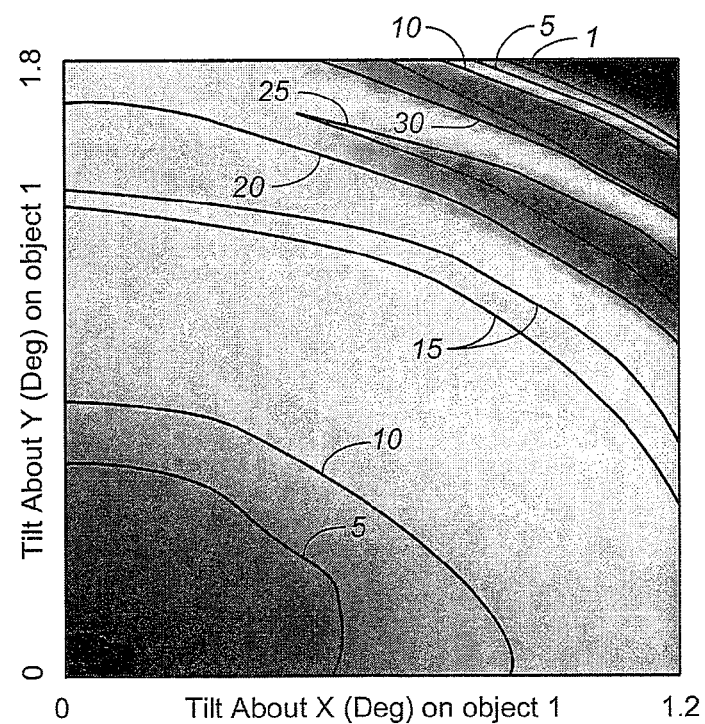
FIG. 3 is a graph showing the number of passes vs. injection angle in a cavity using our invention with a slightly astigmatic exit mirror. In this example, the largely spherical exit mirror has a 1 m radius of curvature, but with 1% astigmatism.

FIG. 3 shows the effect of replacing one or both of the near perfectly spherical mirrors with slightly astigmatic mirrors. In astigmatism, the radius of curvature (and hence the focal length) differs in orthogonal dimensions. A curvature difference or astigmatism of just 1% is sufficient to increase the number of passes by 67% from at most 21 for the perfectly spherical case illustrated by FIG. 2 to at most 35 passes. Again the number of passes depends on tilt angle of the injected beam.

Figure 4:
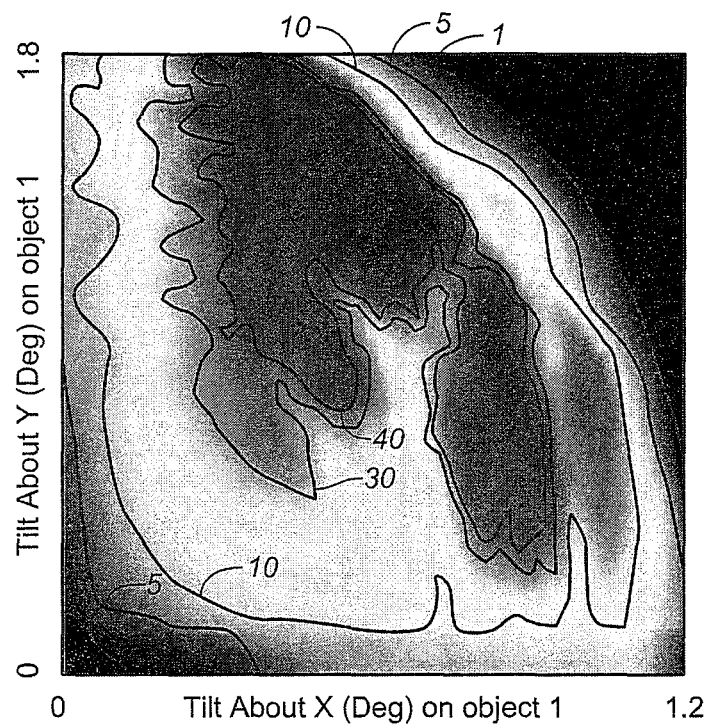
FIG. 4 is a graph showing the number of passes vs. injection angle in a cavity using our invention with a spherical-cylindrical configuration. In this example, the cylindrical exit mirror has a 1 m radius of curvature.
Figure 5:
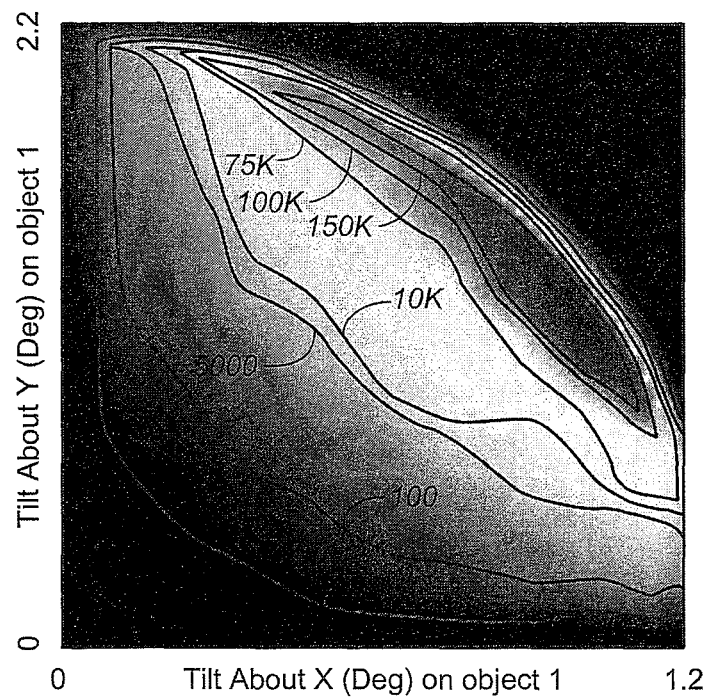
FIG. 5 is a graph showing the number of passes vs. injection angle in a cavity using our invention with an optimized spherical-cylindrical configuration with astigmatism on the spherical mirror. As in FIG. 4, the cylindrical exit mirror has a 1 m radius of curvature.

A preferred configuration for our invention is the spherical-cylindrical cavity, which is not used in any multi-pass cells because as taught in Joel Silver's Applied Optics paper, "Cylindrical-spherical cells have few or no useful allowed reentrant solutions." This fact, which is so detrimental to multi-pass instruments where the beam must be passed out of a hole, we have discovered makes it ideal for use, as in our invention, where the signal is collected entirely through the exit mirror and reentrant conditions rapidly remove light from the cavity leading to shorter path lengths. Relaxation of the reentrant requirement offers the possibility of path lengths much longer than those possible with spherical or astigmatic multipass cells. This effect of employing a spherical-cylindrical configuration is shown in FIG. 4. The spherical-cylindrical configuration offers up to 46 passes. Combining this with the addition of astigmatism in the spherical mirror, an optimized cell can have 300 or more passes, and upwards of many thousands of passes, as seen in FIG. 5.

Low Power Lasers

Quantum cascade lasers (QCL) offer many milliwatts of optical power from 4-10 um. Unfortunately, QCLs cannot access the 3-4 um region where many important hydrocarbons have their strongest absorptions. Inter-band cascade lasers (ICLs) are becoming available but have low power (single milliwatt levels).

QCLs are available beyond 10 um where out-of-plane bending and long chain excitations of complicated organic molecules absorb. However, the emission power of QCLs decreases at longer wavelengths limiting the detection applications that can be accessed with standard CEAS.

Extended range versions of common telecommunications lasers are becoming commercially available that lase beyond 2 um where many interesting overtone absorptions exist. These lasers offer the simple and robust operation of telecom lasers (butterfly packaged, fiber coupled, low current) but also produce only a few milliwatts of power.

Difference frequency generation (DFG) sources are also becoming commercially available. DFGs produce light in the 2-4 um region and, importantly, can be widely tunable. Unfortunately, they typically produce a few microwatts of light.

Although the present invention preferably uses higher power lasers (tens or hundreds of milliwatts) whenever available, the novel cavity configuration now allows the use of such low power lasers, thereby offering a wider range of usable wavelengths.

Poor Mirror Coatings (>8 Um)

Good mirror coatings are preferred, where possible, for longer effective path lengths. However, the cavity configuration of the present invention allows ICOS and other CEAS methods to still be effective even with lower reflectivity mirrors.

Beyond about 8 um, the dielectric materials used to make high reflectivity mirrors (R>99%) must be changed because those used below 8 um have strong absorptions at longer wavelengths. The new materials have smaller but finite absorption that reduce the power delivered to the detector in ICOS and CRDS configurations.

For example Germanium is particularly problematic above 11 um or at high temperature. Operation at high temperature is required in applications that measure "sticky" gases or high molecular weights (i.e., VOCs and semi-VOCs).

Poor Detectors

Because of low laser power and poor mirror coatings, many ICOS instruments in the mid-infrared (MIR) are limited by detector noise. HgCdTe is the material of choice beyond about 6 um and these detectors must be cooled to avoid large thermally induced dark currents. Liquid nitrogen ($LN_2$) cooling produces the lowest noise and thus best instrument sensitivity but is extremely inconvenient ($LN_2$ dewar must be refilled daily; $LN_2$ is not always available; $LN_2$ is mildly hazardous). Thermo-electrically cooled detectors can be used but have higher noise, limiting the utility of some ICOS instruments.

This invention allows the use of high noise detectors, even in a configuration where the system performance would be limited by insufficient power on the detector, for example because of lower power lasers or poor mirror coatings. This is achieved with the present cavity configuration, which increases the power incident on the detector by a factor equal to the front mirror transmission. At the same time, the long path lengths associated with CEAS are largely retained by using an astigmatic cavity to avoid rapidly reentrant conditions and a dramatic decrease in the power retrieved out of the exit mirror.

Multipass Cell Alignment

Problems of low power, poor mirrors, and high noise detectors can be solved using, an astigmatic multipass cell. However, astigmatic multi-pass cells must usually be carefully aligned in prior systems, such that the beam is injected and exits through the cavity hole. Highly skilled practitioners routinely spend hours or days aligning these cells. Additionally, because high pass-count alignments exist for only small injection angle ranges, the systems are very sensitive to temperature and temperature fluctuations as well as to mechanical vibrations.

Many of the practical complications of alignment and stability found in astigmatic multipass cells are avoided in the present invention by removing the requirement that the beam pass back through the entrance hole (or another specific location) with an angle sufficient to physically separate the output from the input beam. Collecting light transmitted through the exit mirror requires only that the multi-pass pattern avoid the entrance hole to the greatest extent possible.

Alternative Embodiments

Partially Transparent Hole: The power to path-length ratio can be altered by using a partial reflective injection hole.

Grin Lens Injection:

The injection can be simplified by using a graded index (GRIN) lens to introduce the light. The GRIN lens can be glued directly into the injection mirror to seal the cell.

Other Fiber Lens Injection:

Alternative collimation lenses such as ball lenses or small molded lenses can be used to collimate a fiber that is embedded in the mirror.

Low Power LEDs:

LEDs may be used in place of lasers with this invention. LEDs in the UV and MIR are potentially useful for absorption spectroscopy but have been avoided because of their low power (microwatts). Although the high pass count alignment cannot be configured as accurately, many of the injected paths will have long path lengths. Injection into long path lengths should be increased by shaping the LED collimation to overlap with the long-path angles, which will have significant planes of symmetry. For instance, an axicon can be used to inject a doughnut shaped beam that overlaps with high pass count angles.

Perfect Injection Mirror:

Ideally the injection mirror will be a perfect reflector. Depending on the light source wavelength, dielectric mirrors can be produced that have transmissions as low at single parts-per-million. A large difference in transmission between injection and exit mirror will bias the escape pathway to the exit mirror, increasing the measurement SNR. This asymmetric configuration isn't available in the standard input/output CEAS configuration because light must be injected and extracted through each mirror.

CRDS:

The method may be used for non-mode matched cavity ringdown although very long ringdown times are precluded.

Off-Axis Injection:

The injection location can be placed off-axis to produce long path lengths with realistic mirrors. Off-axis configurations can be employed with all enumerated mirror configurations to offer more cavity mode structure choices with higher pass counts.

Measured Mirror Surfaces Plus Calculation to Optimize Pattern:

The recent invention described in U.S. Pat. No. 8,531,659 to Silver may be transferred to use with our invention to maximize passes for low cost spherical mirrors.

Walk Off and Return Cavity:

The invention can have a stable cavity configuration in one dimension and a Fabry-Perot cavity in the other dimension. A Fabry-Perot cavity having an introduced non-parallelism away from the injection hole slows and reverses the escape of angled rays.

Other Mirror Shapes:

The shape of each mirror can be adjusted to minimize the proximity of future rays near the injection hole. Cylindrical, conic and even and/or odd aspheric terms can serve this purpose. A specific example is an aspheric mirror where the center is flattened relative to the periphery causing a lower mode density at the center.

What is claimed is:

1. A cavity-enhanced absorption spectroscopy instrument, comprising:
an optical cavity defined by at least two cavity mirrors and containing a sample volume, a first one of the cavity mirrors having an optical aperture formed therein, a same or different one of the cavity mirrors being partially transmissive of light;
a tunable-wavelength light source supplying a light beam directed through the aperture so as to be injected into the optical cavity, at least one of the cavity mirrors being characterized by having an astigmatism such that respective longest and shortest radii of curvature through orthogonal axial planes of that astigmatic mirror differ by at least 1% and selected such that the light beam in the cavity is prevented from exiting the cavity through the aperture until passing in excess of 30 times through the sample volume;
a detector positioned to collect light passing through the partially transmissive cavity mirror; and
a data acquisition and analysis system coupled to the detector and configured to at least determine wavelength-dependent absorption of a sample in the sample volume an integrated cavity output spectroscopy (ICOS) mode or cavity ring-down spectroscopy (CRDS) mode, identify one or more component species present in that sample, and determine a concentration level of the identified component species.

2. The spectroscopy instrument as in claim 1, wherein the optical cavity comprises two mirrors with substantially spherical curvature.

3. The spectroscopy instrument as in claim 1, wherein the optical cavity comprises a first mirror with a substantially spherical curvature and a second mirror with a cylindrical curvature.

4. The spectroscopy instrument as in claim 1, wherein at least one mirror is aspheric and/or conic such that the cavity is characterized by a different optical mode density at the center and periphery of the cavity.

5. The spectroscopy instrument as in claim 1, wherein the aperture is a partially reflective and partially transmissive region of an otherwise highly reflective cavity mirror.

6. The spectroscopy instrument as in claim 1, wherein the first cavity mirror having the aperture is a highly reflective dielectric-coated mirror with a transmissivity less than 10 parts per million except at the aperture.

7. The spectroscopy instrument as in claim 1, wherein the partially transmissive mirror has a reflectivity of at least 98% and a transmissivity of at most 2%.

8. The spectroscopy instrument as in claim 1, wherein the light beam is directed through the aperture at a tilt angle of greater than 0.5° that is selected to maximize number of passes through the sample volume.

9. The spectroscopy instrument as in claim 1, wherein the aperture is located off of a central axis of the optical cavity for off-axis injection of the light beam.

10. The spectroscopy instrument as in claim 1, wherein the optical cavity has mirror curvatures and separation selected such that the optical cavity is a stable cavity.

11. The spectroscopy instrument as in claim 1, wherein the number of passes of the light beam through the sample volume is in excess of 300.

12. The spectroscopy instrument as in claim 1, wherein any one or more of a bare optical fiber, a bare fiber with a collimating element, or a GRIN lens is inserted into the aperture.

13. The spectroscopy instrument as in claim 1, wherein the light source is selected from any one of a quantum cascade laser, an inter-band cascade laser, a supercontinuum laser, and a laser coupled to a difference frequency generator.

14. The spectroscopy instrument in claim 1, wherein the light source is selected from any one of a light emitting diode, super-luminescent diode, thermal bar and broad band light source.

15. The spectroscopy instrument in claim 14, wherein the aperture is removed and the light emitting diode is placed inside the cavity or on the surface of one mirror.

16. The spectroscopy instrument in claim 14, wherein more than one light emitting diode or other broad-band source is used.

17. The spectroscopy instrument as in claim 1, wherein the light beam has a tunable wavelength in a 2 μm to 4 μm range.

18. The spectroscopy instrument as in claim 1, wherein the light beam has a tunable wavelength in a 4 μm to 10 μm range.

19. The spectroscopy instrument as in claim 1, wherein the light beam has a tunable wavelength longer than 10 μm.

20. The spectroscopy instrument as in claim 1, wherein the light beam has a tunable ultraviolet wavelength shorter than 0.46 μm.

21. The spectroscopy instrument as in claim 1, wherein the detector is a mid-infrared detector coupled to a thermoelectric cooler.

22. The spectroscopy instrument as in claim 1, having a pulsed light source and a cavity ring-down mode of operation.

23. The spectroscopy instrument as in claim 1, wherein an angle of light beam injection into the optical cavity, injection off-axis position, mirror rotation, mirror tilt and mirror separation have been computed using a ray tracing model based on measured mirror topography.

* * * * *